United States Patent
Wyllie, II

(10) Patent No.: US 6,257,882 B1
(45) Date of Patent: Jul. 10, 2001

(54) ORTHODONTIC APPLIANCES INCORPORATING CORROSION RESISTANT NICKEL-BASED ALLOY

(75) Inventor: William E. Wyllie, II, Sierra Madre, CA (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 09/420,363

(22) Filed: Oct. 18, 1999

Related U.S. Application Data

(63) Continuation-in-part of application No. 09/175,838, filed on Oct. 19, 1998, now abandoned.

(51) Int. Cl.⁷ .................................................. A61C 3/00
(52) U.S. Cl. ........................................ 433/8; 433/2
(58) Field of Search ............................. 433/2, 8, 9

(56) References Cited

U.S. PATENT DOCUMENTS

| | | | |
|---|---|---|---|
| 3,065,537 | 11/1962 | Knoxville et al. | 228/209 |
| 3,121,629 | 2/1964 | Mann | 420/444 |
| 3,786,565 | 1/1974 | Jarrault | 433/200.1 |
| 3,953,285 | 4/1976 | Martini et al. | 176/66 |
| 3,985,282 | 10/1976 | Miller et al. | 228/175 |
| 4,083,113 | 4/1978 | Miller et al. | 433/17 |
| 4,165,561 | 8/1979 | Miller et al. | 433/9 |
| 4,243,412 | 1/1981 | Tandon | 433/207 |
| 4,283,225 | 8/1981 | Sexton et al. | 428/606 |
| 4,399,096 | 8/1983 | Agarwal et al. | 420/463 |
| 4,448,618 | 5/1984 | Bose et al. | 148/403 |
| 4,508,257 * | 4/1985 | Bose et al. | 228/263.14 |
| 4,591,483 | 5/1986 | Nawaz | 420/463 |
| 4,745,037 | 5/1988 | DeChristofaro et al. | 428/678 |
| 5,018,259 | 5/1991 | Wildman | 29/160.6 |
| 5,088,923 | 2/1992 | Andreiko | 433/9 |
| 5,133,812 | 7/1992 | Kelly et al. | 148/528 |
| 5,154,606 | 10/1992 | Wildman | 433/8 |
| 5,314,109 | 5/1994 | Farzin-Nia | 228/262.42 |
| 5,395,584 | 3/1995 | Berger et al. | 420/443 |
| 5,424,140 | 6/1995 | Rabinkin | 428/606 |
| 5,542,993 | 8/1996 | Rabinkin | 148/528 |
| 5,683,822 | 11/1997 | Hasegawa et al. | 428/606 |
| 5,813,853 | 9/1998 | Kesling | 433/9 |

FOREIGN PATENT DOCUMENTS 2299018  8/1976  (FR).

OTHER PUBLICATIONS

I. Kawakatsu, Welding J. June (1973), pp. 233–239.

Composition and in Vitro Corrosion of Orthodontic Appliances, Copyright 1994–97, Optimedia, Ltd.

E. Lugscheider et al., "Development of Nickel–Chromium–Silicon Base Filler Metals"; Welding Journal including Welding Research, vol. 57, No. 10, Oct. 1978, pp. 319-s–323-s.

* cited by examiner

*Primary Examiner*—John J. Wilson
(74) *Attorney, Agent, or Firm*—James D. Christoff

(57) ABSTRACT

A method of brazing a first component of an orthodontic appliance to a second component of the orthodontic appliance, comprising the step of brazing the first component to the second component using a brazing medium comprising a boron-free brazing alloy that includes at least about 50 weight percent nickel. The brazing alloy of the present invention can also comprise chromium, and/or other elements such as silicon, phosphorous, and/or the like. The method provides strong, corrosion resistant joints with a good color match with stainless steel appliance components.

21 Claims, 1 Drawing Sheet

US 6,257,882 B1

ORTHODONTIC APPLIANCES INCORPORATING CORROSION RESISTANT NICKEL-BASED ALLOY

This application is a continuation-in-part of U.S. patent application Ser. No. 09/175,838, filed Oct. 19, 1998, now abandoned incorporated herein by reference in its entirety.

TECHNICAL FIELD

The present invention is in the field of orthodontic appliances. More specifically, the present invention is in the field of orthodontic appliances in which at least a portion of the components of the appliances are brazed together using a corrosion resistant, nickel-based alloy.

BACKGROUND OF THE INVENTION

In the assembly of components of an orthodontic appliance, e.g., as part of a system commonly referred t o as "races," brazing is often used to bond the components together. Brazing is intended to provide bonds having great strength, temperature resistance, and corrosion resistance.

Brazing refers t o a process of joining metal components, often of dissimilar composition, to each other. Typically, a brazing alloy that has a melting point lower than the melting point of the components to be joined is interposed between the components to form an assembly. The assembly is then heated to a temperature sufficient to melt the brazing, alloy but below the melting point of the components to be joined. The brazing, alloy melts and wets the joint between the components, often by capillary flow of the melted brazing alloy. In some instance, a certain degree of metallurgical reaction might also occur between the brazing alloy and the base metal of the components. Once the joint is wetted, the assembly is cooled so that the brazing alloy solidifies, thus forming a strong bond between the components.

Brazing alloys used in joining, stainless steel components in the orthodontic and dental fields, categorized by the element of highest weight percentage, have been silver-based, gold-based, or nickel-based. In orthodontic and dental applications, the selection of a brazing alloy class impacts the visual aesthetics (e.g,., the color match between the resulting joint and the components), strength, corrosion resistance, and tarnish resistance of the resulting brazed appliance.

Silver-based brazing, alloys are typically alloyed, individually or in combination, with copper, tin, or zinc in order to lower the melting, point of the brazing, alloy. In brazing, stainless steel, silver-based brazing, alloys have the advantage of providing a low melting temperature and good bond strength. However, the color of the brazed joint resulting from the use of silver-based brazing, alloys does not match stainless steel because the brazed joint tarnishes to a dark color over time. Additionally, data suggest that using silver-based brazing alloys that do not include nickel can result in interface corrosion between the base metal of the components and the braze fillet due to nickel depletion at the braze fillet/base metal interface. See, e.g., I. Kawakatsu, Welding J., June (1973) pp. 233–239.

Gold-based brazing alloys are typically alloyed, individually or in combination, with nickel, copper, palladium, and silver. Gold-based brazing, alloys arc often used with stainless steel because gold-based brazing alloys have good strength, ductility, and tarnish resistance. However, the yellow color of gold-based brazing, alloys contrasts with the stainless steel used in the components to be brazed. Moreover, gold is galvanically noble to the active stainless steel along the braze fillet/base metal interface. The galvanic action results in interface corrosion in laboratory tests in physiological saline (Ringer's solution).

Nickel-based brazing, alloys offer an excellent metallic color match to the stainless steel in orthodontic and dental appliances. Conventional nickel-based brazing, alloys are most commonly alloyed with boron in order to lower the melting, point of the brazing, alloy. Chromium also is often present to increase the ductility of the braze fillet while increasing the resistance to high temperature and corrosion. However, under manufacturing or use conditions, the braze joint formed from conventional nickel-based brazing, alloys is preferentially corroded.

What is needed, therefore, is a brazing alloy that has a color that is compatible with the stainless steel used in orthodontic and dental appliances, can form a strong, bond, and is corrosion and tarnish resistant.

SUMMARY OF THE INVENTION

It has now been discovered that the corrosion problem of orthodontic appliances having components brazed together with nickel-based brazements is substantially due to the presence of boron used in these alloys. In the oral cavity, the boron can react with the chromium of the brazement and/or the joined stainless steel components, leaving the braze interface easily corrodible. The strength of the brazed joint also can be weakened.

Accordingly, the present invention is based, at least in part, upon the concept of using boron-free, nickel-based alloys as a brazement for orthodontic assemblies. In preferred embodiments, the alloy may include an agent other than boron that helps to reduce the liquidus temperature of the alloy to allow brazing to occur at conveniently low temperatures. Brazed orthodontic assemblies formed using the boron free, nickel-based alloy of the present invention are highly corrosion resistant, even in harsh saline environments such as Ringer's Solution. The brazement also has good mechanical strength and provides a good color match with stainless steel for good aesthetics. Preferred embodiments also are produced with smooth fillet surfaces by using high heating rates through the melting range of the brazement.

In one aspect, the present invention relates to a method of brazing a first component of an orthodontic appliance to a second component of the orthodontic appliance, comprising the step of brazing the first component to the second component using a brazing medium comprising a boron-free brazing alloy that includes at least about 50 weight percent nickel.

Another aspect of the present invention relates to an orthodontic appliance comprising a first component and a second component, wherein the first and second components are brazed together by a boron-free brazing alloy of the present invention comprising at least about 50 weight percent nickel.

DETAILED DESCRIPTION OF THE INVENTION

The embodiments of the present invention described below are not intended to be exhaustive or to limit the invention to the precise forms disclosed in the following detailed description. Rather the embodiments are chosen and described so that others skilled in the art may appreciate and understand the principles and practices of the present invention.

Figure 1:
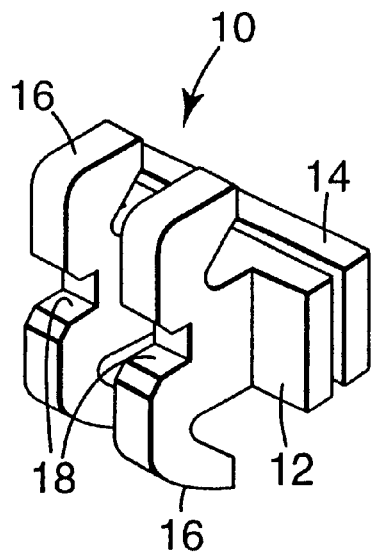
FIG. 1 is a perspective view of an orthodontic appliance before different components of the appliance have been brazed to each other.
Figure 2:
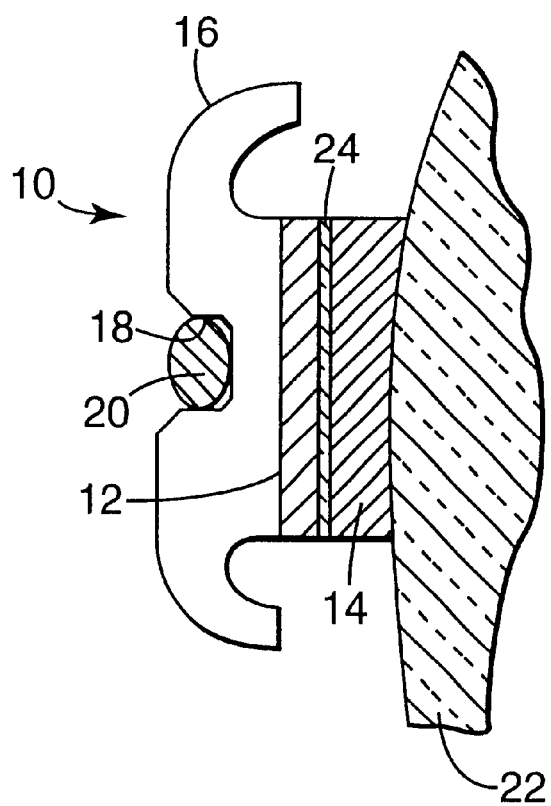
FIG. 2 is a sectional view of the orthodontic appliance of FIG. 1 after the different components of the appliance have been brazed to each other.

An orthodontic bracket 10 of the present invention is shown in FIGS. 1 and 2. Bracket 10 is formed of two major components. These are support member 12 and base member 14. Support member 12 has one or two tiewings 16 in which a slot 18 is formed. Slot 18 is formed with an open side for insertion of an archwire 20 (shown in FIG. 2). The tiewings 16 are provided for connection to a ligating wire or an elastic O-ring that is used to secure archwire 20 in slot 18 of bracket 10. Base member 14 is adapted to be bonded to a tooth 22 (shown in FIG. 2). Although base member 14 is shown in FIG. 2 as a solid member, base member 14 could be formed as a mesh, e.g., a screen or foil or the like, to enhance the mechanical interlock with the adhesive used to bond bracket 10 to tooth 22. Support member 12 and base member 14 preferably comprise stainless steel in order to be impervious to the acids in a patient's mouth. Although the present invention will described in connection with brazing support member 12 and base member 14 together to form brazing fillet 24, it is to be understood that the present invention can be used to form any other brazing joint between orthodontic components, including, but not limited to, brazing joints formed between a hook and the side of bracket 10, between a cap and a buccal tube, between facebow wires, and between a facebow wire and any other component.

In the practice of the present invention, a brazing alloy used to form brazing fillet 24, or any other brazed joint between orthodontic components, is boron-free. In the practice of the present invention, "boron-free" means that the alloy is characterized by a sufficiently low boron concentration to substantially avoid the formation of chromium boride species proximal to the brazed joint. The presence of chromium boride can be detected by sectioning the brazed joint at issue metallographically and then analyzing for chromium boride by electron diffraction. Alternatively, the metallographically sectioned joint can be electrolytically etched in a 10 percent by weight oxalic acid solution with 0.2 amps current for 15 seconds. This preferentially etches chromium depleted regions resulting from chromium boride being formed. After such an etch procedure, the presence of chromium boride is indicated by a relatively dark-colored recess at the braze interface. Preferably, brazed joints of the present invention have a sufficiently low boron content such that the corrosion frequency of such joints is 10% or less, preferably 5% or less, more preferably about 0%. Corrosion frequency, $C_f$, of a joint is given by the expression $$C_f = (N_c / 10)$$

wherein Nc equals the number of corroded joints resulting when 10 stainless steel bracket/base assemblies brazed together using the alloy at issue are stored at 75° C. for 24 hours in Ringer's Solution, then rinsed with deionized water, and then air dried. A joint is corroded when corrosion can be seen at the brazed joint, the base edge proximal to the joint, or the bracket body proximal to the braze joint. Most preferably, the boron content of the brazing alloy of the present invention is less than 0.1%, preferably less than 0.06%, and more preferably less than 0.03% on a weight basis.

Preferred brazing alloys of the present invention further comprise an agent ("$T_L$ reducing agent"), other than boron, that beneficially lowers the liquidus temperature ($T_L$) of the alloy so that brazing can occur at more moderate temperatures, if desired. Representative $T_L$ reducing agents suitable in the practice of the present invention include silicon, phosphorus, manganese, palladium, tin, indium, gallium, gold, germanium, carbon, copper, tungsten, combinations of these, and the like. Of these materials, silicon and phosphorous are more corrosion resistant and, thus, are more preferred.

For example, phosphorous has many advantages when used in a brazing alloy of the present invention. Phosphorous is substantially nonreactive with stainless steel alloys, even in corrosive environments. Thus, boron-free alloys comprising nickel and phosphorous tend to show substantially greater corrosion resistance than alloys that include boron. Thirdly, phosphorous is less mobile than boron in molten alloys in the relatively short time periods typical of brazing operations. This means that phosphorous tends to stay in the brazing alloy, thereby wetting the brazing surfaces of the components to be brazed but not migrating or otherwise penetrating as deeply into the components to be brazed. Therefore, a phosphorous-containing nickel-based brazing alloy will tend to have less of an effect on the bulk properties of the components being brazed than a boron-containing nickel-based brazing alloy.

Silicon is an even more preferred $T_L$ reducing agent than phosphorous and is advantageously incorporated into the brazing alloy either by itself or with other $T_L$ reducing agents such as phosphorous. Not only is silicon corrosion resistant, but it also does not reduce the $T_L$ of the alloy as much as phosphorous. Consequently, brazing alloys containing silicon may still be used to form brazements, but the melting point of such alloys is sufficiently high such that the brazed joint advantageously can be subjected to a post-brazing hardening treatment. Optionally, the $T_L$ reducing agent may incorporate silicon by itself or in combination with one or more other $T_L$ reducing agents.

Preferably, the brazing alloy of the present invention includes a sufficient amount of the $T_L$ reducing agent so that the liquidus temperature of the brazing alloy is suitable for carrying out brazing at the desired temperature. This generally means that the liquidus temperature of the brazing alloy is less than the solidus temperature of the components to be brazed so that the brazing alloy can easily and substantially melt in order to wet the brazing surfaces of the components during brazing without causing the components themselves to melt.

The precise minimum and maximum $T_L$ reducing agent content for a particular brazing alloy will depend upon a variety of factors. As general guidelines, the brazing alloy of the present invention preferably includes about 5 weight percent to about 15 weight percent, more preferably about 10 weight percent, of the $T_L$ reducing agent. Using greater amounts of the $T_L$ reducing agent is not necessarily more beneficial in terms of lowering the liquidus temperature of the alloy. For instance, phosphorous forms a eutectic alloy with nickel, so that adding more phosphorous to a brazing alloy will reduce the melting point of the brazing alloy only up to a certain point, after which additional phosphorous increases the melting point of the alloy. This means that there is generally a minimum and a maximum phosphorous content that can be used to beneficially lower a brazing alloy melting point.

Another preferred embodiment of the brazing alloy of the present invention comprises chromium in addition to nickel and the $T_L$ reducing agent. Although nickel itself is corrosion resistant, nickel-based alloys further comprising chromium are even more corrosion resistant. In addition, chromium also enhances the ductility of the brazing alloy, and chromium and nickel are very compatible with each other in that nickel is an excellent host material for chromium. Generally, a wide range of chromium can be included in the brazing alloy with beneficial results. As a guideline, the brazing alloy of the present invention preferably includes about 5 to 30 weight percent, more preferably about 10 to 25 weight percent, chromium.

One example of a preferred boron-free, nickel-based alloy of the present invention including phosphorous comprises at least about 50 weight percent nickel, less than about 0.03 weight percent boron, about 5 to about 15 weight percent phosphorous, and about 0 to about 30 weight percent chromium. One example of a preferred boron-free, nickel-based alloy of the present invention including silicon comprises about 0 to 30 weight percent chromium, about 5 to 15 weight percent silicon, no more than 0.03 weight percent boron, and the remainder being nickel. Another example of a boron-free, nickel based alloy of the present invention includes at least about 50 weight percent nickel, 3 to 8 weight percent silicon, 10 to 30 weight percent manganese, and about 0 to 6 weight percent copper.

A number of boron-free, nickel-based alloys suitable in the practice of the present invention are commercially available. One such brazing alloy comprises 9 to 11 weight percent phosphorous, 13 to 15 weight percent chromium, 0.2 weight percent iron, 0.08 weight percent carbon, with the balance nickel and is commercially available in powder form as braze 1630 from Fusion, Inc. or Nicrobraz 50 from Wall Colmonoy Corp. Another brazing alloy comprises 9 to 11 weight percent phosphorous, 24 to 26 weight percent chromium, and 0.06 weight percent carbon, with the balance nickel and is commercially available in powder form as Nicrobraz 51 from Wall Colmonoy Corp. Another brazing alloy contains 18.5 to 19.5 weight percent chromium, 9.75 to 10.5 weight percent silicon, 0.10 maximum weight percent carbon and no more than 0.03 weight percent boron, with the balance nickel, and it is available from Fusion, Inc. in powder form as Fusion braze alloy 8100.

The brazing alloys of the present invention may be supplied in any convenient form to carry out the desired brazing operation. For example, the brazing alloy can be a component of a brazing medium in the form of a foil, paste, wire, powder, combinations thereof or the like. The brazing alloys of the present invention can be combined with other, preferably volatile, ingredients to form the brazing medium. The other ingredients preferably are organic so that such ingredients are substantially volatized and thereby removed from the brazing joint during heating in the brazing process. The other ingredients can include fluxes, solvents, binders, and the like that reduce oxidation during brazing, position the brazing alloy on a brazing surface, or otherwise facilitate the brazing process.

A preferred brazing medium is a paste that comprises about 70 to about 90 weight percent of a brazing alloy of the present invention in powder form (preferably having a powder size of U.S. standard sieve −325 F) mixed with about 10 to about 30 weight percent of organic constituents, such as a solvent and a binder. Such a brazing medium can be injected in a controlled fashion onto the brazing surfaces through a needle (such as a hypodermic needle or the like). As another option, a powder form of the brazing alloy can be blended with a neutral liquid binder (such as Fusion CNG commercially available from Fusion, Inc. and S-BINDER commercially available from Wall Colmonoy Corp.) to form a paste that can be applied to the brazing surfaces.

Brazing operations may be carried out in a variety of ways. Generally, the brazing medium initially is positioned at the components to be brazed. Then the components to be brazed arc brought together and heated to a temperature above the melting point of the brazing alloy and below the melting point of the components to be brazed. The brazing alloy melts and wets the brazing surfaces of the components. The components are then allowed to cool so that the brazing alloy hardens and forms a strong joint bond between the two components.

Heating may be carried out in any convenient way, such as in a batch or continuous furnace. It is important to note that many orthodontic appliances are fabricated from components comprising stainless steel, on the surfaces of which chromium oxide tends to form. In order to properly wet such surfaces with the brazing alloy, the chromium oxide is preferably reduced, typically by using a reducing flux or by brazing in a reducing atmosphere such as hydrogen or dissociated ammonia. Also, steps can be taken to inhibit the formation of chromium oxide on the surfaces of the components prior to and after heating by purging oxygen from the surrounding atmosphere. Thus, heating preferably occurs in a continuous furnace comprising an $N_2$ purged gas entry zone, a heating zone having a reducing atmosphere (using a reducing gas like $H_2$ or disassociated ammonia), and an $N_2$ purged gas exit zone.

Regardless of whatever heating apparatus is used, heating should occur for a time sufficient to allow the brazing alloy to melt and wet the brazing joint. If the heating time is too short, the brazing alloy will not properly wet the brazing surfaces and a poor bond will result. Although heating for too long of a time will generally not impair the quality of the resulting bond, heating for too long of a time consumes more resources and time with substantially no benefit. Typical heating time is about 10 seconds to about four hours, preferably about 2 minutes to about 10 minutes.

Heating generally occurs at a temperature above the melting point of the brazing alloy, but less than the melting point of the components to be brazed. Also, the temperature should be hot enough so that the brazing alloy is fluid enough to wet the brazing surfaces of the components to be brazed. For example, a brazing alloy comprising about 75 weight percent nickel, about 11 weight percent phosphorous, about 14 weight percent chromium, and having a liquidus temperature of about 1630° F. may be used to braze stainless steel (having a liquidus temperature of about 2650° F. and a solidus temperature of 2550° F.) at a temperature in the range of about 1630° F. to about 2100° F., preferably in the range of about 1700° F. to about 2000° F.

After heating, the brazed appliance is cooled under conditions sufficient to allow the brazing alloy to harden and form the brazing joint. If the cooling time is too fast, cracking in the brazing joint may result. Also, cooling should occur in a reducing atmosphere at least until the brazed components have cooled sufficiently so as to not oxidize in air. Typical cooling time is about 10 seconds to about 4 hours, preferably about 2 minutes to about 10 minutes.

The heating conditions used during brazing operations can have an effect upon the smoothness of the resulting brazing fillet. Specifically, it has been observed that the heating rate through the melting range of the brazing alloy correlates to fillet smoothness. Generally, use of higher heating rates, e.g., heating rates of about 100° F./min or more, tends to provide smoother fillets. While not wishing to be bound by theory, it is believed that the roughness observed at slower heating rates is due to liquation of the braze.

This effect can be described more concretely in connection with a Ni-19Cr-10Si alloy. This alloy has a lower melting (solidus) temperature of 1079° C. (1975° F.) and an upper melting (liquidus) temperature of 1135° C. (2075° F.). Thus, this particular alloy has a brazing range of 54° C. (100° F.). The alloy will experience liquation if heated too slowly through this melting range. Liquation tends to occur when the low melting part of the material flows away by capillary action, leaving a shell of higher melting material behind.

The type of oven can also affect the smoothness of the brazing fillet. For example, using similar heating profiles, use of a $H_2$ conveyor furnace tends to provide a smoother fillet than does use of a vacuum furnace. Of course, as discussed above, smoother fillets can still be obtained when using a vacuum furnace by increasing the heating rate through the melting range of the brazing alloy.

EXAMPLE 1

Orthodontic brackets were fabricated from a machined stainless steel bracket body and a stainless steel mesh/foil ("base"). For each bracket, a bracket support (or body) and base were tack welded together followed by the application of braze filler metal paste to the joint to be brazed. The paste included a fine metallic powder blended with a neutral organic binder at approximately 75% by weight metal powder. All braze filler metal powders were a −325 mesh (US Standard Sieve) from Fusion, Inc., Willoughby, Ohio with the exception of Ni-P-25Cr powder, which was a −140 mesh (Nicrobraz 51) from Wall Colmonoy Corp., Sterling Heights, Mich. All pastes were blended by Fusion, Inc. using Fusion's proprietary CNG neutral organic binder.

The bracket assemblies were brazed in a reducing atmosphere in a conveyor furnace. The reducing atmosphere was a dry hydrogen retort and commercially pure nitrogen gas blankets were used at the inlet and outlet. Brazing took place at 1890° F.±10° F. (1032° C.±5° C.) for 2 minutes. After brazing, the brackets were tumble-burnished in a chemically neutral burnish solution and water rinsed.

The brackets parts were formed from an AISI type 304L base, a 17-4 PH machined support ("304L/17-4 bracket"), and a braze medium. The braze alloys in the brazing media are listed in Table 1.1 below.

The brackets were tested according to braze type in groups of 10 parts per test cell. Each cell was a vented, polypropylene container containing 35 ml of artificial physiological saline (Ringer's solution). The composition of Ringer's solution is provided in Table 1.2. The test temperature was 75° C. (167° F.). At completion of the 24 hour interval, the test solution was decanted, the brackets were rinsed in distilled water and air dried. Each bracket was viewed with a 5X magnifying lamp. Corrosion indications of "braze joint" type were typically dark red/brown or green coloration on the braze fillet and/or along the perimeter of the braze fillet/stainless steel interface. Indications of corrosion not associated with the braze, e.g., in the base mesh or on the bracket body, were recorded separately. A bracket was only counted once for the most predominant corrosion mode which was observed.

TABLE 1.1

Nominal braze filler metal compositions

| Designation | Vendor Number | Nominal composition, by weight % |
|---|---|---|
| Ni—B—Cr—Si—Fe | Fusion 4777 | 82Ni 7Cr 3B 4.5Si 3Fe 0.06C |
| Ni—P-14Cr | Fusion 1630 | 75Ni 14Cr 10P 0.1B 0.1Si 0.2Fe 0.08C |
| Ni—P-25Cr | Wall Colmonoy Nicrobraz 51 | 65Ni 25Cr 10P 0.1B 0.1Si 0.2Si 0.2Fe 0.06C |
| Ni—P | Fusion 1610 | 89Ni 11P 0.10C |
| Au-18Ni | Fusion 1742 | 82Au 18Ni 0.15Mn |
| Ag—Cu—Ni—Sn | Fusion 4774 | 63Ag 28Cu 2.5Ni 6SN |

TABLE 1.2

Composition of Ringer's solution, with distilled water basis.

| Compound | Concentration (g/L) |
|---|---|
| NaCl | 9.0 |
| KCl | 0.42 |
| $CaCl_2$ | 0.24 |
| $NaHCO_3$ | 0.2 |

Corrosion test results for single test of 10 brackets per braze are presented in Table 1.3. The propensity to corrode at the braze joint is presented by "% Corroded Braze Joint". The "% Corrosion Total" value includes brackets with braze joint corrosion as well as brackets that corroded outside of the braze joint.

Subsequent corrosion testing was performed on a group of commercially available stainless steel, brazed mesh base orthodontic brackets. The general composition of the brazes used for these brackets was recorded, based on quantitative X-ray peak identification in scanning electron microscope—energy dispersive analysis of X-rays (SEM-EDAX). The stainless steels of all brackets are of the austenitic Fe—Cr—Ni—Mo family. Brackets (304L/17-4) with braze Ni-P-14Cr were also included in this test, designated as bracket X30. Five independent test runs of 10 brackets for each bracket were performed and the results were averaged in Table 1.4.

In analyzing the data in Table 1.3, the corrosion resistance of brackets brazed with Ni-P filler metals (Ni-P-14Cr, Ni-P, Ni-P-25Cr) is superior to that of brackets with silver based (Ag—Cu—Ni—Sn), gold (Au-18Ni), or nickel-boron (Ni—B—Cr—Si—Fe). The silver-based brackets suffered a brown-orange tarnishing of the braze fillet. Brackets brazed with Ni—B—Cr—Si—Fe and Au-18Ni exhibited red rust corrosion spots at the braze joint/base metal interface. In contrast, the braze fillets of the Ni-P brazes were bright and unaffected.

Regarding the data in Table 1.4, the brackets brazed with Au—Ni brazes confirm the results in Table 1.3 showing significant corrosion in Ringer's solution when gold-base brazes are used on orthodontic brackets. The brackets brazed with Ag—Cu braze (vendor "C") typically exhibited a red brown rust stain at bracket/braze junction. From this comprehensive data one can conclude that using a boron-free, nickel-phosphorus braze, such as with braze Ni-P-14Cr, minimizes the braze joint corrosion tendency of the stainless steel orthodontic brackets in physiological saline.

TABLE 1.3

Corrosion frequency of stainless steel brazed brackets in 75° C.
Ringer's solution, 24 hours, (sample size: 10 each)

| Bracket | Braze used | % Corroded Braze Joint | % Corroded Total |
|---|---|---|---|
| 304L/17-4 | Ni—B—Cr—Si—Fe | 40 | 100 |
| 304L/17-4 | Au—18Ni | 100 | 100 |
| 304L/17-4 | Agent-Cu—Ni—Sn | 100 | 100 |
| 304L/17-4 | Ni—P—14Cr | 0 | 0 |
| 304L/17-4 | Ni—P | 0 | 0 |
| 304L/17-4 | Ni—P—25Cr | 0 | 10 |

TABLE 1.4

Corrosion frequency of stainless steel brazed brackets in 75° C.
Ringer's solution, 24 hours, Average score of 5 tests with
10 samples in each test.

| Vendor designation | General Braze Composition | % Corroded Braze Joint | % Corroded Total |
|---|---|---|---|
| "A" | Braze Ni B—Cr Si Fe | 24 | 35.5 |
| "B" | Au Ni | 48 | 68 |
| "C" | Ag Cu | 42 | 48 |
| "X30" | Braze Ni—P—14Cr | 2 | 7 |

EXAMPLE 2

In these experiments, brackets formed from an AISI type 304L base and a 17-4 PH machined support ("304L./17-4 bracket") were brazed together. The brazing alloys used to make the bracket samples are listed in Table 2.1 below. To make each bracket sample, a braze paste was applied to the outside of the joint with a hypodermic-tipped syringe. Each braze paste was 75% by weight metal powder (−325 mesh US Standard Sieve) in a neutral organic binder and was obtained from Fusion IEM Incorporated, Willoughby, Ohio.

The brackets were fabricated using the Ni-3B-8Cr-4Si-3Fe brazing alloy (Fusion braze 4777) and were brazed in a dry hydrogen conveyor furnace at a true braze temperature of 1890° F. (1032° C.), at a belt speed of 4 inch/minute (10 cm/minute) and an oven residence time of about 2.5 minutes. The hydrogen supply was −130° F. dewpoint @ 30 SCFIH net in the hot zone.

The brackets were fabricated using the Ni-19Cr-10Si brazing alloy (Fusion braze 8100) and were brazed in a vacuum furnace at $10^{-4}$ torr ($10^{-4}$ mm Hg) at 2100° F.±25° F. (1149° C.±14° C.) for 9 minutes at temperature. Brackets were also formed in vacuum at 2150° F. (1177° C.) and 2200° F. (1204° C.) in tests at 3, 6, and 9 minutes.

Another lot of brackets were also fabricated using the Ni-19Cr-10Si brazing alloy (Fusion braze 8100) in a dry hydrogen conveyor furnace at a true braze temperature of 2100° F. (1149° C.), at a belt speed of 4 inch/minute and a residence time of about 2.5 minutes with the same hydrogen parameters as for the Ni-3B-8Cr-4Si-3Fe brazements.

TABLE 2.1

Nominal braze filler metal compositions.

| Designation | Vendor number | Nominal composition, by weight % |
|---|---|---|
| Ni—3B—8Cr—4Si—3Fe | Fusion 4777 | Ni balance 6.0–8.0Cr 2.75–3.5B 4.0–5.0Si 2.5–3.5Fe 0.06C (max.) |
| Ni—19Cr—10Si | Fusion 8100 | Ni balance 18.5–19.5Cr 9.75–10.5Si 0.03B (max.) |

The brackets were tested according to braze type in groups of 10 parts per test cell. Each cell was a vented, polypropylene container containing 35 ml of artificial physiological saline (Ringer's solution). The composition of Ringer's solution is provided in Example 1. The test temperature was 75° C. (167° F.). At completion of the 24 hour interval, the test solution was decanted, the brackets were rinsed in distilled water and air dried. Each bracket was viewed with a 5X magnifying lamp. Corrosion was rated from 0 to 100%, with the % score (# of brackets with sites corroded/10)×100.

Average corrosion test results are presented in Table 2.3. The corrosion tendency is presented by "%Corroded Braze Joint" and "%Corrosion Total" (which includes brackets with corrosion indications at the braze joint, base edge, or bracket body).

TABLE 2.3

Corrosion frequency of stainless steel brazed brackets in 75° C.
Ringers solution, 24 hours, (Unless otherwise noted, average score
of 5 tests × 10 brackets each)

| Bracket | Braze used | Process, Temperature | % Corroded Braze Joint | % Corroded Total |
|---|---|---|---|---|
| 304L/17-4 | Ni—3B—8Cr—4Si—3Fe | Dry H₂/4 in./min., 1890° F. | 35.5* | 46* |
| 304L/17-4 | Ni—19Cr—10Si | Vacuum ($10^{-4}$ torr)/9 min/2100° F. | 0 | 0 |
| 304L/17-4 | Ni—19Cr—10Si | Vacuum($10^{-4}$ torr)/6 min/2150° F. | 0 | 0 |
| 304L/17-4 | Ni—19Cr—10Si | Vacuum ($10^{-4}$ torr)/3 min/2200° F. | 0 | 0 |
| 304L/17-4 | Ni—19Cr—10Si | Vacuum (10 torr)/9 min/2200° F. | 0 | 0 |
| 304L/17-4 | Ni—19Cr—10Si | Dry H₂/4 in./min., 2100° F. | 0 | 0 |

*Average of 39 tests of ten brackets in each test

In all furnaces, the Ni-19Cr-10Si brazed brackets were resistant to corrosion in the prescribed corrosion test, as all tested brackets exhibited a "zero" score. In contrast the parts brazed with the boron-doped filler, Ni-3B-8Cr-4Si-3Fe, were significantly corroded. The silicon in the Ni-19Cr-10Si diffuses into the stainless steel matrix without preferentially binding the chromium at the braze interface or grain boundaries, as does boron in the Ni-3B-8Cr-4Si-3Fe brazements. In addition to much better corrosion resistance, the parts brazed with Ni-19Cr-10Si in the vacuum or H₂ conveyor processes are as mechanically sound or better than the brackets brazed with Ni-3B-8Cr-4Si-3Fe.

EXAMPLE 3

Referring to the brazements formed in Example 2, it was observed that the Ni-19Cr-10Si parts made in the vacuum furnace had a rough braze fillet compared to the smooth fillets of Ni-3B-8Cr-4Si-3Fe brazements or Ni-19Cr-10Si brazements that were produced in the $H_2$ conveyor furnace. It is believed that the rough fillet can be attributed to liquation of the brazing alloy due to the slow heating rate of the vacuum furnace through the melting range. In contrast, the aesthetically appealing, smooth fillets were formed in the $H_2$ furnace during fast heating through the brazing range.

What is claimed is:

1. A method of brazing a first component of an orthodontic appliance to a second component of the orthodontic appliance, comprising the step of brazing the first component to the second component using a brazing medium comprising a boron-free brazing alloy including at least about 50 weight percent nickel.

2. The method of claim 1, wherein the brazing alloy comprises 0.1 weight percent or less of boron.

3. The method of claim 1, wherein the step of brazing occurs at a temperature in the range from about 1750° F. to 2400° F.

4. The method of claim 1, wherein, during the brazing step, the brazing alloy has a melting range and said brazing alloy is heated at a rate of greater than about 100° F./min over at least a portion of the melting range.

5. The method of claim 1, wherein the brazing alloy further comprises an amount of a $T_L$ reducing agent effective to provide the brazing alloy with a liquidus temperature that is below the solidus temperatures of the first and second components.

6. The method of claim 1, wherein the brazing alloy further comprises chromium.

7. The method of claim 6, wherein the brazing alloy further comprises from about 5 to about 15 weight percent of silicon.

8. The method of claim 6, wherein the brazing alloy further comprises from about 5 to about 15 weight percent of phosphorous.

9. The method of claim 8, wherein the brazing alloy further comprises about 10 weight percent of phosphorous.

10. The method of claim 6, wherein the brazing alloy further comprises from about 5 to about 30 weight percent chromium.

11. The method of claim 6, wherein the first and second components comprise stainless steel.

12. The method of claim 1, wherein a heating rate during the brazing step is sufficiently high to substantially avoid liquation of the brazing alloy.

13. The method of claim 12, wherein said heating rate is predetermined.

14. The method of claim 1, wherein a heating rate during the brazing step is at least 100° F./min.

15. An orthodontic appliance comprising a first component and a second component, wherein the first and second components are brazed together by a boron-free brazing alloy comprising at least about 50 weight percent nickel.

16. The orthodontic appliance of claim 15, wherein the brazing alloy further comprises an amount of a $T_L$ reducing agent effective to provide the brazing alloy with a liquidus temperature that is below the solidus temperatures of the first and second components.

17. The orthodontic appliance of claim 15, wherein the brazing alloy further comprises chromium.

18. The method of claim 17, wherein the brazing alloy further comprises from about 5 to about 15 weight percent of silicon.

19. The method of claim 17, wherein the brazing alloy further comprises from about 5 to about 15 weight percent of phosphorous.

20. The method of claim 17, wherein the brazing alloy further comprises about 10 weight percent of phosphorous.

21. The orthodontic appliance of claim 15, wherein the first and second components comprise stainless steel.

* * * * *

UNITED STATES PATENT AND TRADEMARK OFFICE
CERTIFICATE OF CORRECTION

PATENT NO. : 6,257,882 B1
DATED : July 10, 2001
INVENTOR(S) : William E. Wyllie II Page 1 of 1

It is certified that error appears in the above-identified patent and that said Letters Patent is hereby corrected as shown below:

Column 1,
Line 19, "races" should read -- braces --.
Line 62, "arc" should read -- are --.
Line 65, delete "," following "brazing".

Column 3,
Line 22, insert -- be -- between "will" and "described".

Column 6,
Line 4, "arc" should read -- are --.

Column 10,
Line 49, "10" should read -- $10^{-4}$ --.

Signed and Sealed this

Seventh Day of May, 2002

Attest:

Attesting Officer

JAMES E. ROGAN
*Director of the United States Patent and Trademark Office*